(12) United States Patent
Cowlen et al.

(10) Patent No.: US 7,109,181 B2
(45) Date of Patent: Sep. 19, 2006

(54) JOINT LUBRICATION WITH P2Y PURINERGIC RECEPTOR AGONISTS

(75) Inventors: Matthew S. Cowlen, Chapel Hill, NC (US); Benjamin R. Yerxa, Raleigh, NC (US); Arthur C. Jones, Durham, NC (US); Edward G. Brown, Cary, NC (US)

(73) Assignee: Inspire Pharmaceuticals, Inc., Durham, NC (US)

( * ) Notice: Subject to any disclaimer, the term of this patent is extended or adjusted under 35 U.S.C. 154(b) by 130 days.

(21) Appl. No.: 10/183,320

(22) Filed: Jun. 25, 2002

(65) Prior Publication Data

US 2003/0027785 A1 Feb. 6, 2003

Related U.S. Application Data

(60) Provisional application No. 60/300,942, filed on Jun. 25, 2001.

(51) Int. Cl.
*A61K 31/70* (2006.01)
*A61K 31/66* (2006.01)

(52) U.S. Cl. .................. 514/47; 514/48; 514/52; 514/102; 514/103; 514/140; 514/143

(58) Field of Classification Search ............ 514/52, 514/47, 48, 102, 103, 140, 143, 108, 327, 514/328, 344, 261, 329
See application file for complete search history.

(56) References Cited

U.S. PATENT DOCUMENTS

| | | | |
|---|---|---|---|
| 5,292,498 A | 3/1994 | Boucher, Jr. | 424/45 |
| 5,415,873 A | 5/1995 | Trepel et al. | 424/422 |
| 5,628,984 A | 5/1997 | Boucher, Jr. | 424/45 |
| 5,635,160 A | 6/1997 | Stutts, III et al. | 424/45 |
| 5,656,256 A | 8/1997 | Boucher et al. | 424/45 |
| 5,763,447 A | 6/1998 | Jacobus et al. | 514/265 |
| 5,789,391 A | 8/1998 | Jacobus et al. | 514/51 |
| 5,837,861 A | 11/1998 | Pendergast et al. | 536/25.6 |
| 5,900,407 A | 5/1999 | Yerxa et al. | 514/47 |
| 5,902,567 A | 5/1999 | Boucher, Jr. | 424/9.1 |
| 5,935,555 A | 8/1999 | Stutts, III et al. | 424/45 |
| 5,958,897 A | 9/1999 | Jacobus et al. | 514/49 |
| 5,968,913 A | 10/1999 | LaCroix et al. | 514/47 |
| 5,972,904 A | 10/1999 | Jacobus et al. | 514/51 |
| 5,981,506 A | 11/1999 | Jacobus et al. | 514/47 |
| 5,985,849 A * | 11/1999 | Kindon et al. | 514/51 |
| 6,022,527 A | 2/2000 | Boucher, Jr. et al. | 424/45 |
| 6,133,247 A | 10/2000 | Boucher, Jr. | 514/50 |
| 6,133,434 A * | 10/2000 | Buell et al. | 536/23.5 |
| 6,143,279 A | 11/2000 | Boucher, Jr. et al. | 424/45 |
| 6,323,187 B1 | 11/2001 | Yerxa et al. | 514/51 |

FOREIGN PATENT DOCUMENTS

| | | |
|---|---|---|
| WO | WO94/08593 | 4/1994 |
| WO | WO96/40059 | 12/1996 |
| WO | WO97/05195 | 2/1997 |
| WO | WO97/29756 | 8/1997 |
| WO | WO97/35591 | 10/1997 |
| WO | WO98/03177 | 1/1998 |
| WO | WO98/15835 | 4/1998 |
| WO | WO98/03182 | 5/1998 |
| WO | WO98/19685 | 5/1998 |
| WO | WO98/34593 | 8/1998 |
| WO | WO99/09998 | 3/1999 |
| WO | WO99/32085 | 9/1999 |
| WO | WO99/61012 | 12/1999 |
| WO | WO98/34942 | 1/2000 |
| WO | WO00/30629 | 6/2000 |
| WO | WO00/50024 | 8/2000 |

OTHER PUBLICATIONS

International Search Report filed Nov. 5, 2002.
Benali et al., "Effect of Extracellular ATP and UTP on Fluid Transport by Human Nasal Epithelial Cells in Culture," *Am. J. Respir. Cell. Mol. Biol.* 10:363–368 (1994).
Bora et al., "Joint Physiology, Cartilage Metabolism, and the Etiology of Osteoarthritis," *Hand Clin.* 3:325–336 (1987).
Brown et al., "Evidence that UTP and ATP Regulate Phospholipase C through a Common Extracellular 5'–Nucleotide Receptor in Human Airway Epithelial Cells," *Mol. Pharmacol.* 40:648–655 (1991).
Delecrin et al., "Changes in Joint Fluid After Total Arthroplasty," *Clin. Orthop.* 307:240–249 (1994).
Drutz et al., "Uridine 5' Triphosphate (UTP) Regulates Mucociliary Clearance via Purinergic Receptor Activation," *Drug Dev. Res.* 37(3):185 (1996).
Gobran et al., "$P_{2u}$ Purinoceptor Stimulation of Surfactant Secretion Doubled to Phosphatidylcholine Hydrolysis in Type II Cells," *Am. J. Physiol.* 267:L625–L633 (1994).
Green et al., "Purinergic Regulation of Bradykinin–induced Plasma Extravasation and Adjuvant–induced Arthritis in the Rat," *Proc. Natl. Acad. Sci.*, 88(10):4162–5 (1991).

(Continued)

*Primary Examiner*—Shaojia Anna Jiang
*Assistant Examiner*—Ganapathy Krishnan
(74) *Attorney, Agent, or Firm*—Howrey LLP; Viola T. Kung

(57) ABSTRACT

The present invention is directed to a method of altering the amount or composition of synovial fluids secreted from joints in a subject in need of such treatment. The method comprises administering to a subject a pharmaceutical composition comprising a P2Y purinergic receptor agonist in an amount effective to alter the amount or composition of synovial fluids. The P2Y purinergic receptor agonist is administered in an amount effective to stimulate secretion of synovial fluid, lubricin, hyaluronic acid, or surface-active phospholipids; to enhance joint lubrication; or to treat osteoarthritis. The pharmaceutical compositions useful in the present invention comprise a P2Y purinergic receptor agonist of Formula I and include, but are not limited to: uridine-, adenosine-, cytidine-5'-di- or triphosphates, dinucleoside polyphosphates, and analogs thereof. The invention is useful for treating conditions associated with reduced joint lubrication and joint stiffness, such as osteoarthritis.

19 Claims, 1 Drawing Sheet

OTHER PUBLICATIONS

Hills et al., "Deficiency of Lubricating Subfactant Lining the Articular Sufaces of Replaced Hips and Knees," *Br. J. Rheumatol.* 37:143–147 (1998).

Hills et al., "Boundary Lubrication in vivo," *Proc. Inst. Mech. Eng.* 214:83–94 (2000).

Hosoya et al., "Nucleotide Stimulation of Cl Secretion in the Pigmented Rabbit Conjunctiva," *J. Pharmacol. Exp. Ther.* 291(1):53–59 (1999).

Jay et al., "Characterization of a Bovine Synovial Fluid Lubricating Factor III. The Interaction with Hyaluronic Acid," *Connect. Tissue Res.* 28:245–255 (1992).

Jay et al., "Comparison of the boundary–lubricating ability of bovine synovial fluid, lubricin, and Healon," *J. Biomed. Matl. Res.* 40:414–418 (1998).

Jay et al., "Lubricin Is a Product of Megakaryocyte Stimulating Factor Gene Expression by Human Synovial Fibroblasts," *J. Rheumatol.* 27:594–600 (2000).

Jumblatt et al., "Regulation of Ocular Mucin Secretion by $P2Y_2$ Nucleotide Receptors in Rabbit and Human Conjunctiva," *Exp. Eye Res.* 67:341–346 (1998).

Knowles et al., "Activation by Extracellular Nucleotides of Chloride Secretion in the Airway Epithelia of Patients with Cystic Fibrosis" *New Engl. J. Med.* 325:533–538 (1991).

Lethem et al., "Nucleotide Regulation of Goblet Cells in Human Airway Epithelial Explants: Normal Exocytosis in Cystic Fibrosis," *Am. J. Respir. Cell. Mol. Biol.* 9:315–322 (1993).

Marshall et al., "Intra–articular hyaluronan therapy," *Curr. Opin. Rheumatol.* 12:468–474 (2000).

Mason et al., "Regulation of Transepithelial Ion Transport and Intracellular Calcium by Extracellular ATP in Human Normal and Cystic Fibrosis Airway Epithelium," *Br. J. Pharmacol.* 103:1649–1656 (1991).

Mundasad et al., "Ocular Safety on INS365 Ophthalmic Solution: A $P2Y_2$ Agonist in Healthy Subjects," *J. Ocul. Pharmacol. Ther.* 17(2):173–179 (2001).

Murakami et al., "$P2Y_2$ Receptor Stimulation Increases Tear Fluid Secretion in Rabbits," *Curr. Eye Res.* 21(4):782–787 (2000).

Murakami et al., "$P2Y_2$ Receptor Stimulation Increases Mucin–Like Glycoprotein Secretion from Rabbit Conjunctival Goblet Cells in vivo," *Invest. Ophthalmol. Vis. Sci.* 41(4):S457 (ARVO Abstract 2423 (2000).

Rabinowitz et al., "Lipid Composition of the Tissues of Human Knee Joints," *Clinical Orthopedics and Related Res.* 190:292–298 (1984).

Schwarz et al., "Synovial Surfactant: Lamellar Bodies in Type B Synoviocytes and Proteolipid in Synovial Fluid and the Articular Lining," *Br. J. Rheumatol.* 35:821–827 (1996).

Shiue et al., "Pharmacological Modulation of Fluid Secretion in the Pigmented Rabbit Conjunctiva," *Life Sci.* 66(7):PL105–111 (2000).

Yerxa et al., "$P2Y_2$ Receptor Agonists: Structure, Activity and Therapeutic Utility," *Drugs of the Future* 24(7):759–769 (1999).

Loredo & Benton, "ATP and UTP Activate Calcium–Mobilizing $P_{2U}$–like Receptors and Act Synergistically with Interleukin–1 to Stimulate Prostaglandin $E_2$ Release from Human Rheumatoid Synovial Cells," *Arthritis & Rheumatism* 41:2 pp. 246–255 (1998).

* cited by examiner

JOINT LUBRICATION WITH P2Y PURINERGIC RECEPTOR AGONISTS

This application claims the benefit of U.S. Provisional Application No. 60/300,942, filed Jun. 25, 2001, which is hereby incorporated herein in its entirety by reference.

TECHNICAL FIELD

This invention relates to a method of stimulating the secretion of synovial fluid, mucins, hyaluronic acid, and/or surface-active phospholipids, and thereby enhancing joint lubrication, using P2Y purinergic receptor agonists in patients in need of such treatment.

BACKGROUND OF THE INVENTION

The joint cavity is surrounded by a capsule and held together by ligaments. Synovium lines the joint cavity and is folded upon itself several times to permit considerable motion. The inner portion of the synovium is lined with a layer of synoviocytes, consisting of Type A cells which are involved in phagocytosis and secretion, and Type B cells which are believed to synthesize the hyaluronate of synovial fluid (Bora, et al., Hand Clin. 3: 325–336 (1987)).

Human joints are lubricated by fluid secreted from synovial membranes, which line internal, non-articular joint surfaces. The lubricating properties of synovial fluid have been attributed to a surfactant consisting of surface-active phospholipid (SAPL), the mucinous glycoprotein lubricin, hyaluronic acid (hyaluronan), and water (Schwarz, et al., Br. J. Rheumatol 35: 821–827 (1996), Jay, et al., J. Rheumatol. 27: 594–600 (2000), Marshall, et al., Curr. Opin. Rheumatol. 12: 468–474 (2000), Bora, et al., Hand Clin. 3: 325–336 (1987), Hills, et al., Br. J. Rheumatol. 37: 143–147 (1998), Jay, et al., Connect. Tissue Res. 28: 245–255 (1992), Hills, et al., Proc. Inst. Mech. Eng. 214: 83–94 (2000)). Hyaluronan is a critical constituent component of normal synovial fluid and an important contributor to joint homeostasis. Hyaluronan imparts anti-inflammatory and antinociceptive properties to normal synovial fluid and contributes to joint lubrication, buffering load transmission across articular surfaces and providing a continually replenished source of hyaluronan to articular tissues. (Marshall, Curr. Opin. Rheumatol. 12: 468–474 (2000)).

Joint lubrication is compromised in osteoarthritis (OA) ((Schwarz, et al., Br. J. Rheumatol. 35: 821–827 (1996), Marshall, et al., Curr. Opin. Rheumatol. 12: 468–474 (2000), Hills, et al., Br. J. Rheumatol. 37: 143–147 (1998), Hills, et al., Proc. Inst. Mech. Eng. 214: 83–94 (2000)) and following arthroplastic surgery (Delecrin, et al., Clin. Orthop. 307: 240–249 (1994)). OA is a degenerative joint disease characterized by progressive deterioration and loss of articular cartilage associated with proliferation of new bone and soft tissue in and around the joint. OA can be classified as: (1) primary, in which no underlying cause is apparent; (2) secondary, which is associated with a predisposing factor such as trauma, repetitive stress (occupation, sports), congenital abnormality, metabolic disorder, or other bone/joint disease; and (3) erosive, characterized by hand OA associated with synovitis and radiographic central erosions of the articular surface. Unlike rheumatoid arthritis, a systemic disease simultaneously affecting multiple joints, OA involves only joints that are traumatized or exposed to mechanical abuse. OA develops essentially when the rate of wear exceeds the production of new collagen fibers by chondrocytes. The lipids within the joint, including phospholipid, change in profile shortly after an impact injury leading to eventual OA, whether bone fracture occurs or not (Rabinowitz, et al., Clinical Orthopedics and Related Res. 190: 292–298 (1984)). The following symptoms and criteria are used to establish a diagnosis of osteoarthritis:

Patient History:

Typical symptoms of osteoarthritis include use-related pain affecting one or a few joints with less common rest and nocturnal pain, and brief stiffness after rest or in the morning, lasting less than 30 minutes. Other symptoms include loss of joint movement or functional limitation joint instability, deformity and crepitation ('crackling').

Physical Examination:

Physical examination reveals chronic monarthritis or asymmetric oligo/polyarthritis and firm or "bony" swellings of the joint margins, such as Heberden's or Bouchard's nodes. Patients rarely display synovitis with a cool effusion. On physical examination, crepitance, an audible creaking or crackling of the joints on movement is sometimes detected. Osteoarthritis is also associated with deformity. Patients display restriction of movement, such as the limitation of internal rotation of the hip. Objective neurologic abnormalities are sometimes observed when the spine is involved and affect intervertebral disks, apophyseal joints and paraspinal ligaments.

Laboratory Studies:

Routine laboratory work is normal and conducted to rule out other causes of arthritis such gout, and to detect other primary disorders. Erythrocyte sedimentation rate is normal but is sometimes elevated in patients with synovitis.

Joint Fluid Analysis:

Analysis of the joint fluid provides information about the joint fluid characteristics of osteoarthritis. The joint fluid is normally straw-colored with good viscosity and the number of joint fluid white blood cells (WBC) less than 2000/$\mu$L. Analysis of the joint fluid is important in ruling out crystal-induced arthritis or infection.

X-ray Findings:

As the disease progresses and over a long-term duration, radiographic findings include joint space narrowing, subchondral bone sclerosis, subchondral cysts, and osteophytes. Erosions differ from that characteristic of rheumatoid and psoriatic arthritis because they occur subchondrally along the central portion of the joint surface.

When SAPL is injected into osteoarthritic joints, wear associated with OA is successfully reduced (Hills, Proc. Inst. Mech. Eng. 214: 83–94 (2000)). In OA, the concentration and molecular weight of hyaluronan in synovial fluid is reduced by dilution, fragmentation, and production by synoviocytes of hyaluronan of lower than normal molecular weight. Consequently, the homeostatic condition of synovial fluid maintained by hyaluronan is compromised (Marshall, Curr. Opin. Rheumatol. 12: 468–474 (2000)). The outermost lubricating layer of SAPL deposited onto articular cartilage from synovial fluid is deficient in OA (Hills and Monds, Br. J. Rheumatol. 37: 143–147 (1998)). Studies of changes in joint fluid after total arthroplasty in a rabbit model of total knee replacement have shown that joint fluid volume and total protein concentration recovers to normal, but hyaluronic acid concentration and molecular weight are reduced and do not completely recover to normal values (Delecrin, et al., Clinical Orthopaedics and Related Research 307: 240–249 (1994)).

The recognition that synovial fluid hyaluronan in OA is abnormal led to the proposition that removal of pathologic osteoarthritic synovial fluid and replacement with products that restore the molecular weight and concentration of hyaluronan toward normal levels can have a beneficial therapeutic effect. The treatment approach has been termed viscosupplementation (Marshall, *Curr. Opin. Rheumatol.* 12: 468–474 (2000)). Commercial preparations of hyaluronic acid (Healon), which has joint lubricating qualities, have been used as a viscosupplementation treatment for OA (Jay, et al., *J. Biomed. Matl. Res.* 40: 414–418 (1998)). However, commercial preparations of hyaluronic acid possess inferior lubricating qualities compared with synovial mucin (Jay, et al., *J. Biomed. Matl. Res.* 40: 414–418 (1998)). Pharmacotherapeutic agents used to manage arthritis include analgesics, anti-inflammatory drugs, muscle relaxants, and antidepressants. Aspirin is the drug of choice for both anti-inflammatory and analgesic reasons. Other non-steroidal anti-inflammatory drugs may be used and act by inhibiting lipo-oxygenase conversion of cell membrane lipids to arachidonic acid. Topical capsaicin cream may help to relieve hand or knee pain and acts by causing the release of the peptide substance P from sensory neurons. Muscle relaxants are used usually in low doses and include diazepam, cyclobenzaprine, carisoprodol, and methocarbamol. Although corticosteroids are not administered orally, they can be administered intra-articularly to reduce inflammation and on an intermittent basis to avoid acceleration of cartilage breakdown. However, the crystalline preparations of corticosteroids may cause synovitis. Purely analgesic agents and tricyclic antidepressants for depression may also be useful. However, nonsteroidal anti-inflammatory drugs (NSAIDS) such as ibuprofen and indomethacin, and newer NSAIDs with specificity for cyclooxygenase-2 (COX-2 inhibitors), including celecoxib, are known to induce gastrointestinal toxicity (Mundasad, et al., *J. Ocul. Pharmacol. Ther.,* 17(2): 173–179 (2001)).

As described above, pharmacotherapetuic agents commonly used to treat OA may cause adverse side effects, such as the gastrointestinal toxicity, and do not directly improve joint fluid properties or enhance joint lubrication. There exists a need for agents that are both safe and effective in treating OA by enhancing joint lubrication.

P2Y receptor agonists are known to induce the secretion of mucins, surfactant, and water from respiratory epithelial surfaces in the lung (Yerxa and Johnson, *Drugs Future* 24: 759–769 (1999); Benali, et al., *Am. J. Respir. Cell. Mol. Biol.* 10: 363–368 (1994); Gobran, et al., *Am. J. Physiol.* 267: L625–L633 (1994); Knowles, et al., *New Engl. J. Med.* 325: 533–538 (1991); Lethem, et al., *Am. J. Respir. Cell. Mol. Biol.* 9: 315–322 (1993)). In addition, P2Y receptor agonists induce tear fluid secretion and improve the lubrication and hydration of the ocular surface in dry eye disease by stimulating the release of mucins and water from the conjunctival epithelium (Hosoya, et al., *J. Pharmacol. Exp. Ther.* 291 (1): 53–59 (1999); Murakami, et al., *Invest. Ophthalmol. Vis. Sci.* 41(4): S457 (ARVO Abstract 2423 (2000); Murakami, et al., *Curr. Eye Res.* 21(4): 782–787 (2000); Shiue, et al., *Life Sci.* 66(7): PL105–111 (2000); Jumblatt and Jumblatt, *Exp. Eye Res.* 67: 341–346 (1998)). However, P2Y receptors are not known to have any beneficial affect on the joint or in joint lubrication.

It is also known that P2Y receptor agonists modulate all components of the mucociliary clearance (MCC) system by: (1) increasing both the rate and total amount of mucin secretion by goblet cells in vitro (Lethem, et al., *Am. J. Respir. Cell. Mol. Biol.* 9: 315–22 (1993)); (2) increasing cilia beat frequency in human airway epithelial cells in vitro (Drutz, et al., *Drug Dev. Res.* 37(3): 185 (1996)); (3) increasing Cl⁻ secretion, hence, water secretion from airway epithelial cells in vitro (Mason, et al., *Br. J. Pharmacol.* 103: 1649–1656 (1991); and (4) releasing surfactant from Type II alveolar cells (Gobran, *Am. J. Physiol.* 267: L625–L633 (1994)). In addition to such actions, P2Y agonists have also been shown to increase intracellular $Ca^{++}$ due to stimulation of phospholipase C by the $P2Y_2$ receptor (Brown, et al., *Mol. Pharmacol.* 40: 648–655 (1991); Yerxa and Johnson, *Drugs of the Future* 24(7): 759–769 (1999)). U.S. Pat. Nos. 5,789,391; 5,763,447; 5,635,160; 5,935,555; 5,656,256; 5,628,984; 5,902,567; 5,292,498; 5,837,861; 5,900,407; 5,972,904; 5,981,506; 5,958,897; 5,968,913; 6,022,527; 6,133,247; and 6,143,279, and PCT International Patents WO97/29756, WO97/35591, WO96/40059, WO97/05195, WO94/08593, WO98/19685, WO98/15835, WO98/03182, WO98/03177, WO98/34942, WO98/34593, WO99/09998, WO99/32085, WO99/61012, WO 00/30629, WO 00/50024, and WO96/40059 disclose beneficial therapeutic effects of dinucleotides and related compounds in sinusitis, otitis media, ciliary dyskinesia, pneumonia associated with immobilization, lung disease, cystic fibrosis, dry eye disease, vaginal dryness, bronchitis, edematous retinal disorders, retinal degeneration and detachment, and gastrointestinal disease.

SUMMARY OF THE INVENTION

The present invention is directed to a method of altering the amount or composition of synovial fluids secreted from joints in a subject in need of such treatment. The method comprises administering to a subject a pharmaceutical composition comprising a P2Y purinergic receptor agonist in an amount effective to alter the amount or composition of synovial fluids. The P2Y purinergic receptor agonist is administered in an amount effective to stimulate secretion of synovial fluid, lubricin, hyaluronic acid, or surface-active phospholipids; to enhance joint lubrication, or to treat osteoarthritis. The pharmaceutical compositions useful in the present invention comprise a P2Y purinergic receptor agonist or combination of agonist together with a pharmaceutically acceptable carrier therefor. P2Y purinergic receptor agonists are compounds of Formula I and include, but are not limited to: uridine-, adenosine-, cytidine-5'-di- or triphosphates, dinucleoside polyphosphates, and analogs thereof.

Routes of administration of the pharmaceutical composition include, but are not limited to: topical administration via liquid, cream, gel, ointment, foam, pessary, or tablet; systemic administration via nasal drops or spray, inhalation (nebulizer or other device), oral form (liquid or pill), injectable form, suppository form, or transdermal form; and intra-articular administration by direct injection into the joint cavity. Systemic administration and intra-articular administration can also be accomplished via sustained release, such as by an implanted device.

DETAILED DESCRIPTION OF THE INVENTION

Figure 1:
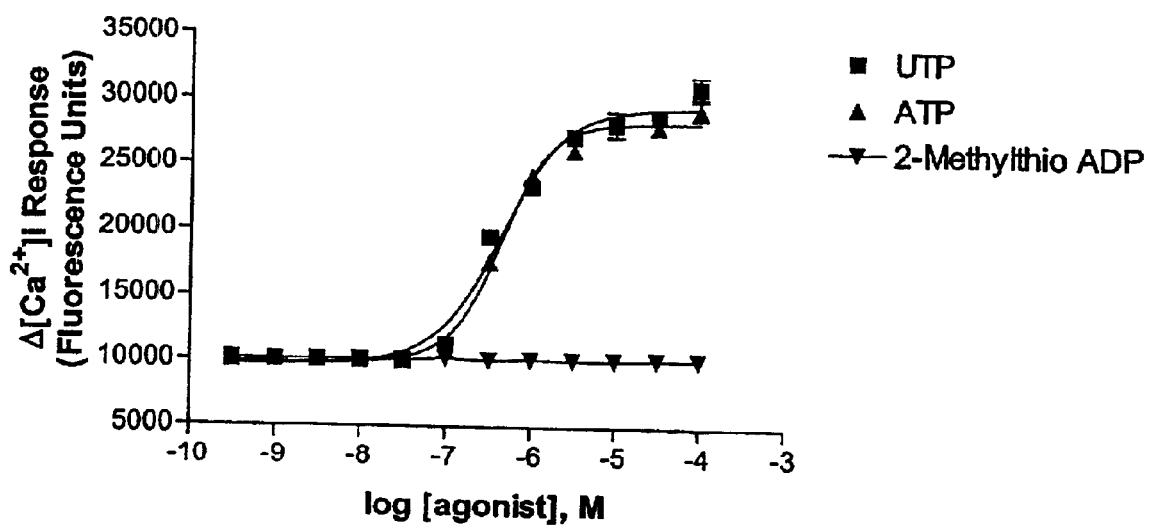
FIG. 1 shows the effects of UTP, ATP and 2-methylthio ADP on cytosolic calcium levels in synoviocytes.

The present invention provides a method of altering the amount or composition of synovial fluids secreted from joints in a subject in need of such treatment. Components that determine the lubricating properties of synovial fluid and can be altered by systemic or local treatment with purinergic receptor agonists include water, mucinous glycoprotein lubricin, hyaluronic acid, and/or surface-active phospholipids. Increasing the amount of, or changing the component ratio in synovial fluids can enhance lubrication in joints, and improve disorders associated with reduced joint secretion and lubrication, such as osteoarthritis and complications of knee and hip replacement. Thus, an embodiment of the present invention is to enhance the secretion of synovial fluid, lubricin, hyaluronic acid, and/or surface-active phospholipids. The method comprises administering to a subject in need thereof a formulation comprising a purinergic receptor agonist or a combination of purinergic receptor agonists in an amount effective to alter the amount or composition of synovial fluids from joints such as knee, hip and shoulder. The P2Y purinergic receptor agonist stimulates P2Y purinergic receptors, which causes the interaction of signaling pathways leading to prosecretory effects.

Another embodiment of the present invention is a method of increasing lubrication in joints by administering a purinergic receptor agonist. Such method provides for the prevention, management and/or treatment of deficiencies of joint secretion and/or lubrication arising from, but not limited to, arthritis, osteoarthritis, joint surgery, knee and hip replacement, and arthroplastic surgery (joint replacement) in mammals, preferably humans.

The methods of the present invention can be used exclusive of, or as an adjunct to, anti-inflammatory and analgesic agents commonly used to treat disorders associated with joint stiffness, such as arthritis. A combined therapeutic approach is beneficial in reducing side effects associated with agents, such as non-steroidal, anti-inflammatory drugs (NSAIDs), commonly used to prevent, manage, or treat disorders such as OA associated with reduced joint lubrication. In addition to enhancing safety, a combined therapeutic approach is also advantageous in increasing efficacy of treatment.

Description of Compounds

P2Y agonists include nucleoside polyphosphates or dinucleoside polyphosphates of general Formula I. Nucleoside triphosphates useful in this application include uridine-5'-triphosphate (UTP), adenosine-5'-triphosphate (ATP), cytidine 5'-triphosphate (CTP) and their analogues of general Formula I; dinucleoside polyphosphates of general Formula I are also useful in this application.

Disclosed are compounds of Formula I:

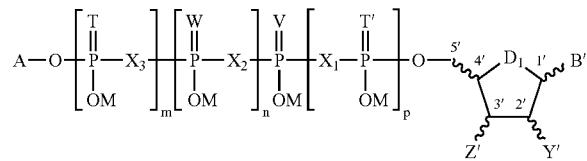

Formula I wherein:
$X_1$, $X_2$, and $X_3$ are independently or together oxygen, methylene, monochloromethylene, dichloromethylene, monofluoromethylene, difluoromethylene, or imido;
T', T, W, and V are independently or together oxygen or sulfur;
m=0, 1 or 2;
n=0 or 1;
p=0, 1, or 2;
where the sum of m+n+p is from 1 to 5;
each M is independently hydrogen or a pharmaceutically-acceptable inorganic or organic counterion;
A=M, alkyl, alkenyl, alkynyl, cycloalkyl, cycloalkenyl, aralkyl, aralkenyl, aralkynyl, aryl, or acylthioalkyl, with or without substituents or heteroatoms; or
A is a nucleoside residue which is defined as:

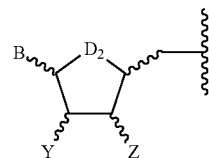

wherein:
$D_1$ and $D_2$ are each independently O or C.
Z and Z' are independently H, $OR_2$ or $OR_3$;
Y and Y' are independently H, F, $OR_1$ or $OR_4$;
independently $R_1$, $R_2$, $R_3$, and $R_4$ is H, or a residue according to Formula II, provided that at least one $R_1$, $R_2$, $R_3$, or $R_4$ is H;

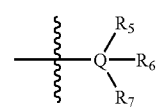

Formula II wherein:
Q is a carbon atom;
$R_5$, $R_6$, and $R_7$ are independently H, alkyl, cycloalkyl, aralkyl, aryl, substituted aralkyl, substituted aryl, or heterocyclic moiety, or $R_5$ and $R_6$ are taken together to form a carbocyclic or heterocyclic ring of 4 to 7 members, such that the moiety defined according to Formula II is an ether; or
provided that $R_5$ and $R_6$ are taken together as oxygen or sulfur doubly bonded to Q, and $R_7$ is alkyl, cycloalkyl, aralkyl, substituted aralkyl, aryl, substituted aryl, or a heterocycle of 4 to 7 members, such that the moiety defined according to Formula II is an ester or thioester; or
provided that $R_5$ and $R_6$ are taken together as oxygen or sulfur doubly bonded to Q, and $R_7$ is amino or mono- or disubstituted amino, where the substituents are alkyl, cycloalkyl, aralkyl, aryl, substituted aralkyl, or substituted aryl, or where the substituents on nitrogen form a heterocyclic ring of 4 to 7 members such that the moiety according to Formula II is a carbamate or thiocarbamate; or
provided that $R_5$ and $R_6$ are taken together as oxygen or sulfur doubly bonded to Q, and $R_7$ is alkoxy, cycloalkoxy, aralkyloxy, aryloxy, substituted aralkyloxy, or substituted aryloxy, such that the moiety according to Formula II is a carbonate or thiocarbonate;
B and B' are independently a purine or a pyrimidine residue according to Formulae III or IV which is linked to the 1'-position of the furanose or carbocycle via the 9-position of the purine or the 1-position of the pyrimidine.

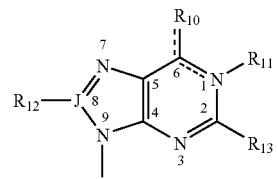

Formula III

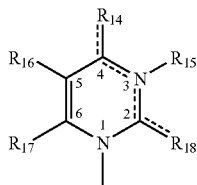

Formula IV wherein:
R$_{10}$ and R$_{14}$ are independently CN, N$_3$, hydroxy, oxo, amino, mercapto, alkylthio, alkoxy, aryloxy, alkylamino, cycloalkylamino, aralkylamino, arylamino, diaralkylamino, diarylamino, N-alkyl-N-arylamino, or dialkylamino, where the alkyl and/or aryl groups are optionally linked to form a heterocycle; or R$_{10}$ and R$_{14}$ are independently acylamino, according to Formula V;

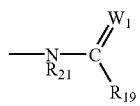

Formula V or, when R$_{10}$ or R$_{14}$ has as its first atom nitrogen, R$_{10}$ and R$_{11}$ or R$_{14}$ and R$_{15}$ are optionally taken together as —CH=CH— to form a 5-membered, fused imidazole ring (an etheno compound), optionally substituted on the imidazole ring of the etheno-compound with substituted- or unsubstituted- alkyl, cycloalkyl, aralkyl, or aryl moieties;

J is carbon or nitrogen, with the provision that when J is nitrogen, R$_{12}$ is not present;

R$_{11}$ is hydrogen, O (adenine 1-oxide derivatives) or is absent (adenine derivatives);

R$_{12}$, when present, is hydrogen, alkyl, azido, amino, alkylamino, arylamino, aralkylamino, dialkylamino, diarylamino, diaralkylamino, N-alkyl-N-arylamino, N-alkyl-N-aralkylamino, N-aralkyl-N-arylamino, hydroxy, alkoxy, aryloxy or aralkyloxy, sulfhydryl, alkylthio, arythio or aralkylthio, or ω-X(C$_{1-6}$alkyl)G-, wherein X is substituted- or unsubstituted- amino, mercapto, hydroxy or carboxyl, and G is chosen from —O— (to give an ether), —S— (to give a thioether), —NR$_{20}$— (to give an amine), —N(CO)R$_{20}$— (to give an amide), or N(CO)OR$_{22}$ (to give a carbamate);

R$_{13}$ is hydrogen, chlorine, fluorine, hydroxy, alkoxy, aryloxy, aralkykoxy, amino, monosubstituted amino, disubstituted amino, alkylthio, trifluoroalkylthio, arylthio, or aralkylthio, where the substituent on sulfur contains up to a maximum of 20 carbon atoms, with or without unsaturation;

R$_{15}$ is hydrogen, or acyl (e.g. acetyl, benzoyl, phenylacyl, with or without substituents);

R$_{16}$ is hydrogen, methyl, substituted- or unsubstituted-alkyl, halo, aryl, aralkyl, alkenyl, substituted alkenyl, alkynyl, or substituted alkynyl;

R$_{17}$ is halogen, hydrogen, alkoxy or is an acylamino group according to Formula V; or R$_{16}$ and R$_{17}$, when taken together, represent a ring of 5 to 7 members, with or without heteroatoms or substituents;

R$_{18}$ is hydrogen, oxo, alkoxy, amino, alkylamino, arylamino, aralkylamino, dialkylamino, diarylamino, arylalkylamino, arylaralkylamino, alkylaralkylamino, sulfhydryl, alkylthio, arythio, aralkylthio, or acylamino according to Formula V;

R$_{19}$ is amino or mono- or disubstituted amino such that the moiety according to Formula V is a urea or thiourea; or R$_{19}$ is alkoxy, aralkyloxy or aryloxy, such that the moiety according to Formula V is a carbamate or thiocarbamate; or R$_{19}$ is hydrogen, alkyl, cycloalkyl, aralkyl, or aryl, with or without substituents or heteroatoms, such that the moiety according to Formula V is an amide or thioamide;

R$_{20}$ and R$_{21}$ independently are hydrogen, alkyl, cycloalkyl, aralkyl, or aryl, with or without substituents or heteroatoms;

R$_{22}$ is alkyl, cycloalkyl, aralkyl, or aryl, with or without substituents or heteroatoms; and W$_1$ is oxygen or sulfur.

When D$_1$ and D$_2$ are oxygen, the furanosyl moieties of Formula I independently can be in the D-configuration or in the L-, or both in the D- and L-configurations. The D-configuration is preferred. Each nucleoside residue independently can be in the alpha- or beta-configuration, but most preferably is in the beta-D-configuration. The furanosyl moieties can include ribofuranosyl, 2'-deoxyribofuranosyl, 3'-deoxyribofuranosyl, 2',3'-dideoxyribofuranosyl, arabinofuranosyl, 3'-deoxyarabinofuranosyl, xylofuranosyl, 2'-deoxyxylofuranosyl, and lyxofuranosyl derivatives, with the ribofuranosyl and the 2'-deoxyribofuransoyl moieties being preferred.

In the general structure of Formula III, the dotted lines are intended to indicate the presence of single or double bonds in these positions; the relative positions of the double or single bonds being determined by whether the R$_{10}$ and R$_{11}$ substituents are capable of keto-enol tautomerism.

In the general structure of Formula IV, the dotted lines in the 2- to 4-positions are intended to indicate the presence of single or double bonds in these positions; the relative positions of the double or single bonds being determined by whether the R$_{14}$, R$_{15}$, and R$_{18}$ substituents are capable of keto-enol tautomerism. When R$_{14}$ is double-bonded from an oxygen or sulfur atom to the carbon at the 4-position of the pyrimidine ring, R$_{15}$ is hydrogen.

As used herein, the term "alkyl" refers to C$_{1-10}$ inclusive, linear, branched, or cyclic, saturated or unsaturated (i.e., alkenyl and alkynyl) hydrocarbon chains, for example, methyl, ethyl, propyl, isopropyl, butyl, isobutyl, tert-butyl, pentyl, hexyl, octyl, ethenyl, propenyl, butenyl, pentenyl, hexenyl, octenyl, butadienyl, propynyl, butynyl, pentynyl, hexynyl, heptynyl, allenyl and optionally substituted aryalkenyl and arylalkynyl groups. As used herein, the term "acyl" refers to an organic acid group wherein the —OH of the carboxyl group has been replaced with another substituent (i.e., as represented by X'CO— or X'CS—, wherein X' is a hydrogen, an alkyl, an aralkyl, an aryl, an alkoxy, an aryloxy, an aralkoxy, an amino, N-substituted amino or an N,N-disubstituted amino group). As such, the term "acyl" specifically includes arylacyl groups. Specific examples of acyl groups include acetyl and benzoyl. As used herein, the term "aryl" refers to carbocyclic and heterocyclic aromatic groups of 5 to 12 ring atoms. Examples of aryl groups include phenyl, naphthyl, furan, thiophene, pyrrole, pyridine, imidazole, isothiazole, isoxazole, pyrazole, pyrazine, and the like. The term "alkoxy" as used herein refers to C$_{1-10}$ inclusive, linear, branched, or cyclic, saturated or unsaturated hydrocarbon chains bonded to an oxygen atom. This includes, for example, methoxy, ethoxy, propoxy, isopropoxy, butoxy, t-butoxy, and decyloxy. The term "aryloxy" as used herein refers to groups such as phenyloxy, as well as alkyl-, halo-, and/or alkoxy-substituted aryloxy groups. The term "thioalkyl" as used herein refers to $C_{1-10}$ inclusive linear, branched, cyclic, saturated or unsaturated hydrocarbon chains bonded to a sulfur atom. This includes, for example, thiomethyl, thioethyl, thiopropyl, thioisopropyl, thiobutyl, thio-t-butyl, and thiodecyl. The term "thioaryl" as used herein refers to groups such as thiophenyl, as well as alkyl-, halo-, and/or alkoxy-substituted thioaryl groups. As used herein, the terms "substituted alkyl" and "substituted aryl" include alkyl and aryl groups, as defined herein, in which one or more atoms or functional groups of the aryl or alkyl group are replaced with another atom or functional group, such as halogen, aryl, alkyl, alkoxy, hydroxy, nitro, amino, alkylamino, dialkylamino, sulfate, and thioalkyl. The terms "halo," "halide," or "halogen" as used herein refer to fluoro, chloro, bromo, and iodo groups.

Compounds illustrative of those of Formula I include those disclosed in WO 99/09998; the reference is incorporated herein by reference. Formula I compounds, for example, include: $P_1$, $P_4$-diadenosinetetraphosphate ($A_2P_4$); uridine-5'-diphosphate (UDP); uridine-5'O(2-thiodiphosphate)(UDPβS); 5-bromouridine-5'-triphosphate (5-BrUTP); 5-(1-phenylethynyl)-uridine-5'triphosphate (5-(1-phenylethynyl)UTP); 5-methyluridine-5'-diphosphate (5-methylUDP); 4-hexylthiouridine-5'-triphosphate (4-hexylthioUTP); 4-thiouridine-5'-triphosphate (4-thioUTP); 2-methoxyuridine-5'-triphosphate (2-methoxyUTP); 4-(1-morpholino)uridine-5'-tetraphopsphate (4-(1-morpholino))$UP_4$; 4-hexyloxyuridine-5'-diphosphate (4-hexyloxyUDP); 4-(N,N-dimethyl)cytidine-5'-triphosphate (N, N-dimethylCTP); 4-(N-hexyl)cytidine -5'-triphosphate (N-hexylCTP); $P^1$-(cytidine-5')-$P^4$-(uridine-5'-)tetraphosphate ($CP_4U$); $P^1$-O-(methyl)-$P^4$-(uridine-5'-)tetraphosphate ($MeP_4U$) and 4-(N-cyclopentyl)thymidine-5'-triphopsphate (N-cyclopentylCTP).

Preferred compounds of Formula I include 5'-adenosine-triphosphate (ATP), 5'-uridine-triphosphate (UTP), uridine-5'-O-(3-thiotriphosphate)(UTPγS) and $P^1$-(uridine-5')-$P^4$-(uridine-5'-) tetraphosphate ($U_2P_4$). Particularly preferred compounds of Formula I include 5'-[4-(thiouridine)]-triphosphate (4-thioUTP) and $P^1$-(cytidine-5')-$P^4$-(uridine-5'-) tetraphosphate ($CP_4U$). Certain compounds of Formula I (e.g., UTP, dUDP, ATPγS, and 4-thioUDP) are known and can be made in accordance with known procedures or variations thereof, which will be apparent to those skilled in the art. For example, the identification and preparation of certain thiophosphate analogues of nucleoside diphosphates (such as UDP-β-S) are set forth in U.S. Pat. No. 3,846,402 and Goody and Eckstein (*J. Am. Chem. Soc.* 93: 6252–6257 (1971)). Alternatively, UTP, and other analogs thereof are also commercially available from vendors such as Sigma (St. Louis, Mo.) and Pharmacia (Uppsala, Sweden).

One embodiment of the present invention is a method of using a hydrolysis-resistant agonist. A hydrolysis-resistant agonist is a nucleotide with a modified phosphate ester backbone, e.g. a methylene, imido or other group, or some other structural modification that protects the phosphate ester and/or phosphate anhydride bonds from being readily hydrolyzed. Another embodiment is a method of using a dinucleoside polyphosphate, which is also resistant to hydrolysis due to a lack of a terminal phosphate group. Certain dinucleoside polyphosphates are especially resistant to hydrolysis. For example, $P^1$-(cytidine-5')-$P^4$-(uridine-5'-) tetraphosphate is more resistant in comparison with $P^1$, $P^4$-Di(uridine-5'-)tetraphosphate. Furthermore, groups placed on the end of the phosphate chain impart some stability against hydrolysis, e.g. simple alkyl phosphate esters (methyl, ethyl, benzyl, etc.) or thiophosphate derivatives (e.g. UTPγS) hydrolyze more slowly. Many P2Y agonists are dinucleotides or dinucleotide analogues, and many of these are particularly active at $P2Y_2$ receptors. Dinucleoside polyphosphates of general Formula I are useful in this application. Thus, yet another preferred embodiment of the present invention is a method of stimulating secretions in an affected joint using $P2Y_2$ receptor agonists.

Compounds encompassed by the present invention can be prepared by condensation of a nucleoside mono-, di-, or triphosphate, activated with a condensing agent such as, but not limited to, carbonyldiimidazole or dicyclohexylcarbodiimide, with a second molecule of the same or a different mono-, di-, or triphosphate to form the desired dinucleoside polyphosphate. Another method of preparation is the sequential condensation of a nucleoside phosphate, activated as above, with a non-nucleoside mono-, di- or polyphosphate moiety such as, but not limited to, a monophosphate or pyrophosphate anion to yield the desired dinucleoside polyphosphate, the non-isolated intermediate in such a case being a mononucleoside polyphosphate. Yet another preparative approach is the sequential condensation of a mono-, di- or polyphosphate moiety, activated as mentioned above, or in the form of an acid halide or other derivative reactive toward nucleophilic displacement, with a nucleoside phosphate or polyphosphate to yield the desired dinucleoside polyphosphate. The desired dinucleoside polyphosphate can be formed by modification of a pre-formed dinucleoside polyphosphate by substitution or derivatization of a moiety or moieties on the purine, pyrimidine or carbohydrate rings. Nucleoside phosphates used as starting materials may be commercially available, or they can be made from the corresponding nucleosides by methods well known to those skilled in the art. Likewise, where nucleosides are not commercially available, they can be made by modification of other readily available nucleosides, or by synthesis from heterocyclic and carbohydrate precursors by methods well known to those skilled in the art.

Those having skill in the art will recognize that the starting materials can be varied and additional steps employed to produce compounds encompassed by the present invention. In some cases protection of certain reactive functionalities may be necessary to achieve some of the above transformations. In general, the need for such protecting groups will be apparent to those skilled in the art of organic synthesis as well as the conditions necessary to attach and remove such groups.

The compounds of the present invention also encompass their non-toxic pharmaceutically acceptable salts, such as, but not limited to, an alkali metal salt such as lithium, sodium or potassium; an alkaline earth metal salt such as magnesium or calcium; or an ammonium or tetraalkyl ammonium salt, i.e., $NL_4^+$ (wherein L is $C_{1-4}$), with the monovalent salts such as lithium, sodium, potassium, and ammonium being most preferred. Pharmaceutically acceptable salts are salts that retain the desired biological activity of the parent compound and do not impart undesired toxicological effects. The present invention also encompasses the acylated prodrugs of the compounds disclosed herein. Those skilled in the art will recognize various synthetic methodologies which can be employed to prepare non-toxic pharmaceutically acceptable salts and acylated prodrugs of the compounds (International Patent Nos. WO 96/40059, WO 96/02554A1, WO-A-9815563, and WO 98/55494; Theoclitou, et al., *J. Chem. Soc. Perkin Trans.* I, 2009–2019 (1996); Guranowski, et al., *Nucleosides and Nucleotides* 14, 731–734 (1995); Visscher, et al., *Nucleic Acids Research* 20, 5749–5752 (1992); Holler, et al., *Biochemistry* 22, 4924–4933 (1983); Orr, et al., *Biochem. Pharmacol.* 673–677 (1988); Plateau, et al., *Biochemistry* 24, 914–922 (1985); Hagmeier, et al., *J. Chromatography* 237, 174–177 (1982); Scheffzek, et al., *Biochemistry* 35, 9716–9727 (1996); Stridh, et al., *Antiviral Res.*, 97–105 (1981); Tarasova, et al., *Chem. Abs.* 110, 154770 (1988); Hata, et al., *Chem Lett.*, 987–990 (1976); Huhn, et at., 28, 1959–1970 (1993); Tumanov, et al., *Chem. Abs.* 109–6867d (1987); Pintor, et al., *Molecular Pharmacology* 51, 277–284 (1997); and U.S. Pat. Nos. 4,855,304; 5,635,160; 5,495,550; and 5,681,823).

The pharmaceutical utility of compounds of this invention is indicated by the cytosolic calcium assay for $P2Y_2$ and other P2Y receptor activity. This widely used assay, as described in Pendergast, et al. (2001) (*Bioorg. Med. Chem. Lett.* 11, 157–160), relies on the measurement of increased cytosolic calcium levels to determine the biological activity of compounds that activate receptors linked via G-proteins to phospholipase C. The efficacy of these compounds is reflected in their ability to alter and/or enhance the secretory activity of the joints, including but not limited to, the knee, hip, and shoulder, to effectuate the agent's target response. The target response is the improvement of joint lubrication and movement.

Dosage levels of the order of from about $10^{-7}$ M to about $10^{-1}$ M, preferably in the range $10^{-5}$ to $10^{-1}$M, are useful in the treatment of the above-indicated conditions, including disorders of joint lubrication. The effective dose ranges between about 0.1 to about 1000 mg, preferably between about 0.1 to about 100 mg, and most preferably between about 0.5 to about 50 mg for single doses. The amount of active ingredients that can be combined with the carrier materials to produce a single dosage form will vary depending upon the host treated and the particular mode of administration. It will be understood, however, that the specific dose level for any particular patient will depend upon a variety of factors, including the activity of the specific compound employed, the age, body weight, general health, sex, diet, time of administration, route of administration, and rate of excretion, drug combination and the severity of the particular disease in the patient undergoing therapy, and can be determined by those skilled in the art.

Though the compounds of the present invention are primarily concerned with the treatment of human subjects, they can also be employed for the treatment of other mammalian subjects such as dogs, cats and horses for veterinary purposes.

The compounds disclosed herein can be administered to the joint of a patient by any suitable means, such as by topical, intra-articular injection or systemic administration. Topical administration includes the use of a solution, gel, suspension, cream, or ointment containing the active compound in a physiologically compatible vehicle. Gels or jellies can be produced using a suitable gelling agent including, but not limited to, gelatin, tragacanth, or a cellulose derivative and can include glycerol as a humectant, emollient, and preservative. Ointments are semi-solid preparations that consist of the active ingredient incorporated into a fatty, waxy, or synthetic base. Examples of suitable creams include, but are not limited to, water-in-oil and oil-in-water emulsions. Water-in-oil creams can be formulated by using a suitable emulsifying agent with properties similar to emulsifying wax, or similar to those of the fatty alcohols, such as cetyl alcohol or cetostearyl alcohol. Oil-in-water creams can be formulated using an emulsifying agent such as cetomacrogol emulsifying wax. Suitable properties include the ability to modify the viscosity of the emulsion and both physical and chemical stability over a wide range of pH. The water soluble or miscible cream base can contain a preservative system and can also be buffered to maintain an acceptable physiological pH.

Alternatively, the active compounds can be administered by a continuous release device. Those skilled in the art of delivery system development can select using conventional criteria. Solutions formulated for administration to the joint are usually referred to as irrigations. These are sterile solutions, prepared in a manner typical of sterile injections that are intended as a single use sterile solution.

Foam preparations can be formulated to be delivered from a pressurized aerosol canister, via a suitable applicator, using inert propellants. Suitable excipients for the formulation of the foam base include, but are not limited to, propylene glycol, emulsifying wax, cetyl alcohol, and glyceryl stearate. Potential preservatives include methylparaben and propylparaben.

Another method of topical administration is by delivery through the vagina. Pessaries are solid unit-dose forms suitably shaped for insertion into the vagina and can either be composed of a base that melts at body temperature or which dissolves when in contact with mucous secretions. Examples of suitable bases include, but are not limited to, theobroma oil, synthetic fat bases (e.g. Witepsol), polyethylene glycols (macrogols), and glycerol suppository bases. Vaginal tablets are composed of the active ingredient contained within a solid dosage form base which can include, but not be limited to, excipients such as lactose, microcrystalline cellulose, corn starch, magnesium stearate, silicon dioxide, and hydroxypropyl methylcellulose.

Another means of administration of the active compound to the synovial tissues of the subject involves intra-articular injection of the active compound, such that a therapeutically effective amount of the compound reaches the synovial tissues locally.

A further means of administration of the active compounds is systemically via various methods. One such means involves an aerosol suspension of respirable particles comprised of the active compound, which the subject inhales. The active compound is absorbed into the bloodstream via the lungs and contacts the synovial tissues in a pharmaceutically effective amount. The respirable particles can be liquid or solid, with a particle size sufficiently small to pass through the mouth and larynx upon inhalation; in general, particles ranging from about 1 to 10 microns, but more preferably 1–5 microns in size are considered respirable.

Another means of systemically administering the active compounds to the synovial tissues of the subject involve administering a liquid/liquid suspension in the form of nasal drops of a liquid formulation, or a nasal spray of respirable particles that the subject inhales. Liquid pharmaceutical compositions of the active compound for producing a nasal spray or nasal drops are prepared by combining the active compound with a suitable vehicle, such as sterile pyrogen free water or sterile saline by techniques known to those skilled in the art.

Other means of systemic administration of the active compound involve oral administration, in which pharmaceutical compositions containing a compound or compounds of Formula I are in the form of tablets, lozenges, aqueous or oily suspensions, dispersible powders or granules, emulsion, hard or soft capsules, or syrups or elixirs. Compositions intended for oral use can be prepared according to any method known to the art; such compositions can contain one or more agents selected from the group consisting of sweetening agents, flavoring agents, coloring agents, and preserving agents in order to provide pharmaceutically elegant and palatable preparations. Tablets can be prepared to contain the active ingredient in admixture with nontoxic pharmaceutically acceptable excipients that are suitable for the manufacture of tablets. These excipients can be, for example, inert diluents, such as calcium carbonate, sodium carbonate, lactose, calcium phosphate, or sodium phosphate; granulating and disintegrating agents, for example, corn starch or alginic acid; binding agents, for example, starch, gelatin, or acacia; and lubricating agents, for example magnesium stearate, stearic acid, or talc. The tablets can be uncoated or they can be coated by known techniques to delay disintegration and absorption in the gastrointestinal tract and thereby provide a sustained action over a longer period. For example, a time delay material such as glyceryl monostearate or glyceryl distearate can be employed. Formulations for oral use can also be presented as hard gelatin capsules wherein the active ingredient is mixed with an inert solid diluent, for example, calcium carbonate, calcium phosphate, or kaolin, or as soft gelatin capsules wherein the active ingredient is mixed with water or an oil medium, for example, peanut oil, liquid paraffin, or olive oil.

The active compounds can also be delivered to a subject through absorption by the skin using transdermal patches or pads. The active compounds are absorbed into the bloodstream through the skin. Plasma concentrations of the active compounds can be controlled using patches containing different levels of active compounds.

Additional means of systemic administration of the active compound to the synovial tissues of the subject involve a suppository form of the active compound, such that a therapeutically effective amount of the compound reaches the synovial tissues via systemic absorption and circulation.

The invention is illustrated further by the following examples of treatment, which are not to be construed as limiting the scope or spirit to the specific procedures described in them.

EXAMPLE 1

Measurement of Cytosolic Calcium in Cultured Synovial Fibroblasts

A conventional technique was used to detect increases in cytosolic calcium induced by P2Y receptor agonists, a technique familiar to those skilled in the art. Cells were seeded in 96-well plates and used for cytosolic calcium assays. On the day of the assay, the growth medium was aspirated and replaced with a solution of Fluo-3 AM (2.5 µM final concentration) in an assay buffer consisting of (mM): KCl (10), NaCl (118), $CaCl_2$ (2.5), $MgCl_2$ (1), HEPES (20), glucose (10), pH 7.4. Probenecid (Sigma Chemical Co.) was added to the dye load and dye wash medium at a working concentration of 2.5 mM to increase dye retention in the cells. After a 60 minute incubation with Fluo-3 AM at 25° C., cells were washed free of dye (Columbus Plate Washer, TECAN U.S., Inc., Research Triangle Park, N.C.) and were stimulated with increasing concentrations of P2Y receptor agonists. Intracellular calcium levels were simultaneously monitored in each well by measuring the changes in fluorescence intensity using the FLIPR (Molecular Devices Corp., Sunnyvale, Calif.).

Synovial fibroblasts were subjected to the cytosolic calcium assay described above. The results show that the P2Y receptor agonists ATP and UTP stimulate increases in cytosolic calcium in these cells, consistent with activation of the $P2Y_2$ receptors in synoviocytes (FIG. 1). 2-methylthioADP, a $P2Y_1$ receptor-selective agonist, did not alter cytosolic calcium concentration in synovial fibroblasts, indicating the lack of $P2Y_1$ receptors in these cells. The induction of increases in cytosolic calcium by ATP and UTP in synovial fibroblasts indicated the pharmaceutical utility of $P2Y_2$ receptor agonists in the joint.

EXAMPLE 2

Effects of Purinergic Receptor Agonist in Patients with Osteoarthritis

A formulation of a pharmaceutical composition that is a purinergic receptor agonist of Formula I, together with a pharmaceutically acceptable carrier, is prepared as a sterile solution for administration by intra-articular injection. This formulation is administered to patients to achieve a joint fluid concentration in the range of $10^{-7}$ M to $10^{-1}$ M. Patients demonstration typical clinical manifestastions of osteoarthritis are diagnosis and selected for treatment on the basis of pattern of joint involvement, radiographic features, laboratory tests, and synovial fluid findings. At baseline and after treatment with the formulation, the patients undergo examinations including history, physical examinations by specialists, routine laboratory studies, radiographic assessment, and analysis of joint fluid.

Criteria for Therapeutic Efficacy

One of the criteria for determining the effectiveness of treatment with the formulation is the normalization of at least one joint fluid characteristic, including but not limited to synovial fluid coloration, viscosity and a WBC count of less than 2,000/µL. In patients with synovitis, normalization of erythrocyte sedimentation rate is another criteria for determining the effectiveness of treatment. Alternative criteria are the improvement of joint movement, including a decrease in joint stiffness, less restriction of joint rotation, and/or a reduction in crepitation, improvement in radiographic (x-ray) findings including reduction of joint space narrowing, subchondral bone sclerosis, subchondral cysts, and osteophytes, and a reduction in joint pain. The formulation improves at least one of the above symptoms or criteria.

The invention and the manner and process of making and using it are now described in such full, clear, concise and exact terms as to enable any person skilled in the art to which it pertains, to make and use the same. It is to be understood that the foregoing describes preferred embodiments of the present invention and that modifications can be made therein without departing from the spirit or scope of the present invention as set forth in the claims. To particularly point out and distinctly claim the subject matter regarded as invention, the following claims conclude this specification.

What is claimed is:

1. A method of altering the amount or composition of synovial fluids secreted from joints in a subject in need of such treatment comprising:

administering to a subject a pharmaceutical composition comprising a P2Y purinergic receptor agonist in an amount therapeutically effective to alter the amount or composition of synovial fluids, wherein said P2Y purinergic receptor agonist is administered to achieve a joint fluid concentration range of about $10^{-7}$ M to about $10^{-1}$ M, and said P2Y purinergic receptor agonist is a nucleoside polyphosphate of Formula I:

Formula I

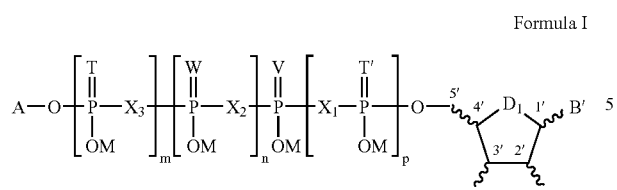

wherein:
- $X_1$, $X_2$, and $X_3$ are independently or together oxygen, methylene, monochloromethylene, dichloromethylene, monofluoromethylene, difluoromethylene, or imido;
- T, T', W, and V are independently or together oxygen or sulfur;
- m=0, 1 or 2;
- n=0 or 1;
- p=0, 1, or 2;
- where the sum of m+n+p is from 1 to 5;
- each M is independently hydrogen or a pharmaceutically-acceptable inorganic or organic counterion;
- A=M, alkyl, alkenyl, alkynyl, cycloalkyl, cycloalkenyl, aralkyl, aralkenyl, aralkynyl, aryl, or acylthioalkyl, with or without substituents or heteroatoms; or
- A is a nucleoside residue defined as:

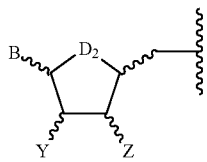

wherein:
- $D_1$ and $D_2$ are each independently O or C;
- Z and Z' are independently H, $OR_2$ or $OR_3$;
- Y and Y' are independently H, F, $OR_1$ or $OR_4$;
- independently $R_1$, $R_2$, $R_3$, and $R_4$ is H, or a residue according to Formula II, provided that at least one $R_1$, $R_2$, $R_3$, or $R_4$ is H;

Formula II

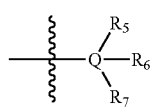

wherein:
- Q is a carbon atom;
- $R_5$, $R_6$, and $R_7$ are independently H, substituted or unsubstituted alkyl, alkenyl, alkynyl, cycloalkyl, cycloalkenyl, aralkyl, aralkenyl, aralkynyl, aryl, or heterocyclic moiety, or
- $R_5$ and $R_6$ are taken together to form a carbocyclic or heterocyclic ring of 4 to 7 members, such that the moiety defined according to Formula II is an ether; or
- provided that $R_5$ and $R_6$ are taken together as oxygen or sulfur doubly bonded to Q, and $R_7$ is substituted or unsubstituted alkyl, alkenyl, alkynyl, cycloalkyl, cycloalkenyl, aralkyl, aralkenyl, aralkynyl, or a heterocycle of 4 to 7 members, such that the moiety defined according to Formula II is an ester or thioester; or
- provided that $R_5$ and $R_6$ are taken together as oxygen or sulfur doubly bonded to Q, and $R_7$ is amino or mono- or disubstituted amino, where the substituents are alkyl, cycloalkyl, aralkyl, aryl, substituted aralkyl, or substituted aryl, or where the substituents on nitrogen form a heterocyclic ring of 4 to 7 members such that the moiety according to Formula II is a carbamate or thiocarbamate; or
- provided that $R_5$ and $R_6$ are taken together as oxygen or sulfur doubly bonded to Q, and $R_7$ is alkoxy, cycloalkoxy, aralkyloxy, aryloxy, substituted aralkyloxy, or substituted aryloxy, such that the moiety according to Formula II is a carbonate or thiocarbonate;
- B and B' are independently a purine or a pyrimidine residue according to Formulae III or IV which is linked to the 1'-position of the furanose or carbocycle via the 9-position of the purine or the 1-position of the pyrimidine;

Formula III

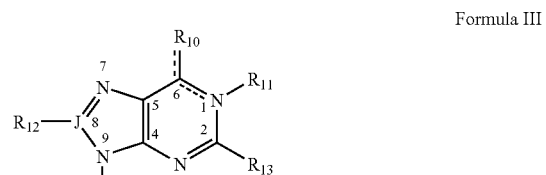

Formula IV

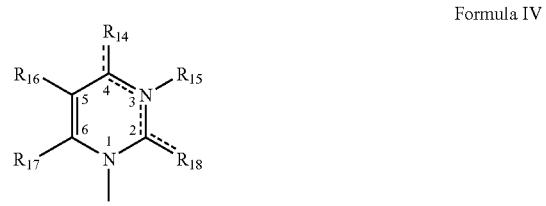

wherein:
- $R_{10}$ and $R_{14}$ are independently CN, $N_3$, hydroxy, oxo, amino, mercapto, alkylthio, alkoxy, aryloxy, alkylamino, cycloalkylamino, aralkylamino, arylamino, diaralkylamino, diarylamino, N-alkyl-N-arylamino, or dialkylamino, where the alkyl and/or aryl groups are optionally linked to form a heterocycle; or
- $R_{10}$ and $R_{14}$ are independently acylamino, according to Formula V;

Formula V

or when $R_{10}$ or $R_{14}$ has as its first atom nitrogen, $R_{10}$ and $R_{11}$ or $R_{14}$ and $R_{15}$ are taken together as —CH=CH— to form a 5-membered, fused imidazole ring, optionally substituted on the imidazole ring with substituted- or unsubstituted- alkyl, cycloalkyl, aralkyl, or aryl moieties; J is carbon or nitrogen, with the provision that when J is nitrogen, $R_{12}$ is not present; $R_{11}$ is hydrogen, O, or is absent;

$R_{12}$, when present, is hydrogen, alkyl, azido, amino, alkylamino, arylamino, aralkylamino, dialkylamino, diarylamino, diaralkylamino, N-alkyl-N-arylamino, N-alkyl-N-aralkylamino, N-aralkyl-N-arylamino, hydroxy, alkoxy, aryloxy or aralkyloxy, sulfhydryl, alkylthio, arythio or aralkylthio, or ω-X($C_{1-6}$alkyl)G- wherein X is substituted- or unsubstituted- amino, mercapto, hydroxy or carboxyl, and G is —O—,—S—,—NR$_{20}$—,—N(CO)R$_{20}$—, or N(CO)OR$_{22}$;

R$_{13}$ is hydrogen, chlorine, fluorine, hydroxy, alkoxy, aryloxy, aralkykoxy, amino, monosubstituted amino, disubstituted amino, alkylthio, trifluoroalkylthio, arylthio, or aralkylthio, where the substituent on sulfur contains up to a maximum of 20 carbon atoms, with or without unsaturation;

R$_{15}$ is hydrogen, or acyl with or without substituents;

R$_{16}$ is hydrogen, methyl, substituted- or unsubstituted-alkyl, halo, aryl, aralkyl, alkenyl, substituted alkenyl, alkynyl, or substituted alkynyl;

R$_{17}$ is halogen, hydrogen, alkoxy or is an acylamino group according to Formula V; or R$_{16}$ and R$_{17}$, when taken together, represent a ring of 5 to 7 members, with or without heteroatoms or substituents;

R$_{18}$ is hydrogen, oxo, alkoxy, amino, alkylamino, arylamino, aralkylamino, dialkylamino, diarylamino, arylalkylamino, arylaralkylamino, alkylaralkylamino, sulfhydryl, alkylthio, arythio, aralkylthio, or acylamino according to Formula V;

R$_{19}$ is amino or mono- or disubstituted amino such that the moiety according to Formula V is a urea or thiourea; or R$_{19}$ is alkoxy, aralkyloxy or aryloxy, such that the moiety according to Formula V is a carbamate or thiocarbamate; or R$_{19}$ is hydrogen, alkyl, alkenyl, alkynyl, cycloalkyl, cycloalkenyl, aralkyl, aralkenyl, aralkynyl, with or without substituents or heteroatoms, such that the moiety according to Formula V is an amide or thioamide;

R$_{20}$ and R$_{21}$ independently are hydrogen, alkyl, cycloalkyl, aralkyl, or aryl, with or without substituents or heteroatoms;

R$_{22}$ is alkyl, cycloalkyl, aralkyl, or aryl, with or without substituents or heteroatoms; and W$_1$ is oxygen or sulfur.

2. A method according to claim 1, wherein said P2Y purinergic receptor agonist is administered in an amount therapeutically effective to affect a response selected from the group consisting of: enhancing joint lubrication, and stimulating secretions of synovial fluids, lubricin, hyaluronic acid, or surface-active phospholipid.

3. The method according to claim 1, wherein at least one of the sugar moieties of said nucleoside polyphosphate is selected from the group consisting of: ribofuranosyl, 2'-deoxyribofuranosyl, 3'-deoxyfuranosyl, 2',3'-dideoxyribofuranosyl, arabinofuranosyl, 3'-deoxyarabinofuranosyl, xylofuranosyl, 2'-deoxyxylofuranosyl and lyxofuranosyl.

4. The method according to claim 1, wherein said nucleoside polyphosphate is selected from the group consisting of nucleoside diphosphates, nucleoside triphosphates, and dinucleoside polyphosphates.

5. The method according to claim 4, wherein said nucleoside polyphosphate is selected from the group consisting of uridine-5'-diphosphate, adenosine-5'-diphosphate, cytidine-5'-diphosphate, uridine-5'-triphosphate, adenosine-5'-triphosphate, cytidine-5'-triphosphate, and ethenocytidine-5'-triphosphate.

6. The method according to claim 1, wherein said pharmaceutical composition is a sterile formulation that further comprises a pharmaceutically suitable carrier.

7. The method according to claim 1, wherein said joint fluid concentration range is about 10$^{-5}$ to 10$^{-1}$ M.

8. The method according to claim 1, wherein said nucleoside polyphosphate is co-administered with an existing therapeutic agent for managing arthritis.

9. The method according to claim 8, wherein said existing therapeutic agent is selected from the group consisting of an analgesic agent, anti-inflammatory agent, muscle relaxant, anti-depressant, and an agent that promotes joint lubrication.

10. The method according to claim 1, wherein said administering is topical administration of said pharmaceutical composition.

11. The method according to claim 10, wherein said pharmaceutical composition is administered in a form of a solution, a gel, a suspension, a cream, an ointment, a foam, a pessary or a tablet.

12. The method according to claim 1, wherein said administering is systemic or local administration of said pharmaceutical composition.

13. The method according to claim 12, wherein said systemic administration is administering to said subject said pharmaceutical composition in a form selected from the group consisting of: an aerosol suspension of respirable particles; a liquid or liquid suspension for administration as nose drops or nasal spray; a nebulized liquid for administration to oral or nasopharyngeal airways; an oral form; a suppository form; an injectable form; and a transdermal patch or a transdermal pad; such that a therapeutically effective amount of said compound contacts the synovial tissues of said subject via systemic absorption and circulation.

14. The method according to claim 12, wherein said local administration is administering to said subject said pharmaceutical composition in an injectable form for local intra-articular administration to the affected joint.

15. A method for treating osteoarthritis, comprising the step of administering to a subject a pharmaceutical composition comprising a purinergic receptor agonist in an amount therapeutically effective to alter the amount or composition of synovial fluids, wherein said pharmaceutical composition is administered to achieve a joint fluid concentration range of about 10–7 M to about 10–1 M, and said purinergic receptor agonist is a nucleoside polyphosphate of Formula I according to claim 1.

16. A method of altering the amount or composition of synovial fluids secreted from joints in a subject in need of such treatment comprising:

administering to a subject a P2Y purinergic receptor agonist in an amount therapeutically effective to alter the amount or composition of synovial fluids, said P2Y purinergic receptor agonist is a dinucleoside polyphosphate of Formula I:

Formula I

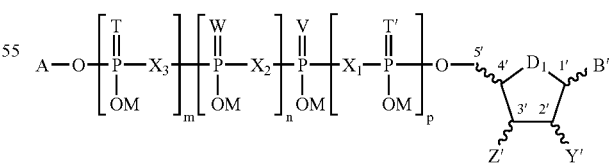

wherein: X$_1$, X$_2$, and X$_3$ are independently or together oxygen, methylene, monochloromethylene, dichloromethylene, monofluoromethylene, difluoromethylene, or imido;

T, T', W, and V are independently or together oxygen or sulfur;

m=0, 1 or 2;

n=0 or 1;

p=0, 1, or 2;

where the sum of m+n+p is from 1 to 5;

each M is independently hydrogen or a pharmaceutically-acceptable inorganic or organic counterion;

A is a nucleoside residue defined as:

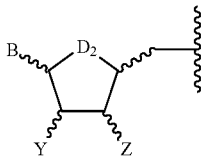

wherein:

D$_1$ and D$_2$ are each independently O or C;

Z and Z' are independently H, OR$_2$ or OR$_3$;

Y and Y' are independently H, F, OR$_1$ or OR$_4$; independently R$_1$, R$_2$, R$_3$, and R$_4$ is H, or a residue according to Formula II, provided that at least one R$_1$, R$_2$, R$_3$, or R$_4$ is H;

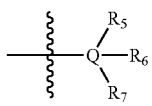

Formula II wherein:

Q is a carbon atom;

R$_5$, R$_6$, and R$_7$ are independently H, substituted or unsubstituted alkyl, alkenyl, alkynyl, cycloalkyl, cycloalkenyl, aralkyl, aralkenyl, aralkynyl, aryl, or heterocyclic moiety, or R$_5$ and R$_6$ are taken together to form a carbocyclic or heterocyclic ring of 4 to 7 members, such that the moiety defined according to Formula II is an ether; or provided that R$_5$ and R$_6$ are taken together as oxygen or sulfur doubly bonded to Q, and R$_7$ is substituted or unsubstituted alkyl, alkenyl, alkynyl, cycloalkyl, cycloalkenyl, aralkyl, aralkenyl, aralkynyl, or a heterocycic of 4 to 7 members, such that the moiety defined according to Formula II is an ester or thioester; or provided that R$_5$ and R$_6$ are taken together as oxygen or sulfur doubly bonded to Q, and R$_7$ is amino or mono- or disubstituted amino, where the substituents are alkyl, cycloalkyl, aralkyl, aryl, substituted aralkyl, or substituted aryl, or where the substituents on nitrogen form a heterocyclic ring of 4 to 7 members such that the moiety according to Formula II is a carbamate or thiocarbamate; or provided that R$_5$ and R$_6$ are taken together as oxygen or sulfur doubly bonded to Q, and R$_7$ is alkoxy, cycloalkoxy, aralkyloxy, aryloxy, substituted aralkyloxy, or substituted aryloxy, such that the moiety according to Formula II is a carbonate or thiocarbonate;

B and B' are independently a purine or a pyrimidine residue according to Formulae III or IV which is linked to the 1'-position of the furanose or carbocycle via the 9-position of the purine or the 1-position of the pyrimidine;

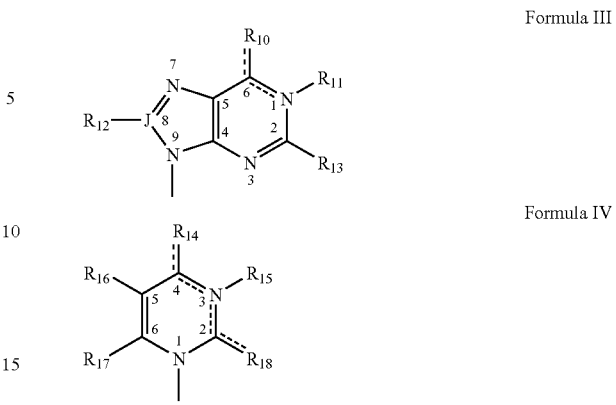

Formula III

Formula IV

Formula V wherein:

R$_{10}$ and R$_{14}$ are independently CN, N$_3$, hydroxy, oxo, amino, mercapto, alkylthio, alkoxy, aryloxy, alkylamino, cycloalkylamino, aralkylamino, arylamino, diaralkylamino, diarylamino, N-alkyl-N-arylamino, or dialkylamino, where the alkyl and/or aryl groups are optionally linked to form a heterocycle; or R$_{10}$ and R$_{14}$ are independently acylamino, according to Formula V;

or when R$_{10}$ or R$_{14}$ has as its first atom nitrogen, R$_{10}$ and R$_{11}$ or R$_{14}$ and R$_{15}$ are taken together as —CH=CH— to form a 5-membered, fused imidazole ring, optionally substituted on the imidazole ring with substituted- or unsubstituted- alkyl, cycloalkyl, aralkyl, or aryl moieties;

J is carbon or nitrogen, with the provision that when J is nitrogen, R$_{12}$ is not present;

R$_{11}$ is hydrogen, O, or is absent;

R$_{12}$, when present, is hydrogen, alkyl, azido, amino, alkylamino, arylamino, aralkylamino, dialkylamino, diarylamino, diaralkylamino, N-alkyl-N-arylamino, N-alkyl-N-aralkylamino, N-aralkyl-N-arylamino, hydroxy, alkoxy, aryloxy or aralkyloxy, sulfhydryl, alkylthio, arythio or aralkylthio, or ω-X(C$_{1-6}$alkyl)G— wherein X is substituted- or unsubstituted- amino, mercapto, hydroxy or carboxyl, and G is —O—,—S—,—NR$_{20}$—,—N(CO)R$_{20}$—, or N(CO)OR$_{22}$;

R$_{13}$ is hydrogen, chlorine, fluorine, hydroxy, alkoxy, aryloxy, aralkykoxy, amino, monosubstituted amino, disubstituted amino, alkylthio, trifluoroalkylthio, arylthio, or aralkylthio, where the substituent on sulfur contains up to a maximum of 20 carbon atoms, with or without unsaturation;

R$_{15}$ is hydrogen, or acyl with or without substituents;

R$_{16}$ is hydrogen, methyl, substituted- or unsubstituted-alkyl, halo, aryl, aralkyl, alkenyl, substituted alkenyl, alkynyl, or substituted alkynyl;

R$_{17}$ is halogen, hydrogen, alkoxy or is an acylamino group according to Formula V; or R$_{16}$ and R$_{17}$, when taken together, represent a ring of 5 to 7 members, with or without heteroatoms or substituents;

$R_{18}$ is hydrogen, oxo, alkoxy, amino, alkylamino, arylamino, aralkylamino, dialkylamino, diarylamino, arylalkylamino, arylaralkylamino, alkylaralkylamino, sulfhydryl, alkylthio, arythio, aralkylthio, or acylamino according to Formula V;

$R_{19}$ is amino or mono- or disubstituted amino such that the moiety according to Formula V is a urea or thiourea; or $R_{19}$ is alkoxy, aralkyloxy or aryloxy, such that the moiety according to Formula V is a carbamate or thiocarbamate; or $R_{19}$ is hydrogen, alkyl, alkenyl, alkynyl, cycloalkyl, cycloalkenyl, aralkyl, aralkenyl, aralkynyl, with or without substituents or heteroateoms, such that the moiety according to formula v is an amide or thioamide;

$R_{20}$ and $R_{21}$ independently are hydrogen, alkyl, cycloalkyl, aralkyl, or aryl, with or without substituents or heteroatoms;

$R_{22}$ is alkyl, cycloalkyl, aralkyl, or aryl, with or without substituents or heteroatoms; and $W_1$ is oxygen or sulfur.

17. The method according to claim 16, wherein said dinucleoside polyphosphates of general Formula I are dinucleoside tetraphosphates selected from the group consisting of $P^1,P^4$-di(uridine-5'-)tetraphosphate; $P^1$-(cytidine-5'-) $P^4$-(uridine-5')tetraphosphate; $P^1,P^4$-di(adenosine-5'-) tetraphosphate; $P^1$-(adenosine-5'-)$P^4$-(uridine-5'-) tetraphosphate; $P^1$-(adenosine-5'-)$P^4$-(cytidine-5') tetraphosphate; $P^1,P^4$-di(ethenoadenosine)tetraphosphate; $P^1$-(uridine-5'-)$P^4$-(thymidine-5'-)tetraphosphate; $P^1$-(adenosine-5'-) $P^4$-(inosine-5'-)tetraphosphate; $P^1,P^4$-di(uridine-5'-)$P^2,P^3$-methylenetetraphosphate; $P^1,P^4$-di(uridine-5'-)$P^2,P^3$-difluoromethylenetetraphosphate; $P^1,P^4$-di(uridine-5'-)$P^2,P^3$-imidotetraphosphate; $P^1,P^4$-di(4-thiouridine-5'-) tetraphosphate; $P^1,P^4$-di(3,N$^4$-ethenocytidine-5'-)tetraphosphate; $P^1,P^4$-di(imidazo[1,2-c]pyrimidine-5(6H)-one-2-(3-nitrophenyl)-6-β-D-ribofuranoside-5'-) tetraphosphate; $P^1$-(inosine-5'-)P4-(uridine-5'-) tetraphosphate; $P^1$-(4-thiouridine-5'-)$P^4$-(uridine-5'-)tetraphosphate; $P^1$-(cytosine-β-D-arabinofuranoside-5-) $P^4$-(uridine-5'-)tetraphosphate; $P^1$-(uridine-5'-)$P^4$-(xanthosine-5'-) tetraphosphate; $P^1$-(2'-deoxyuridine-5'-)$P^4$-(uridine-5'-)tetraphospbate; $P^1$-(3'-azido-3'-dexoythymidine-5'-) $P^4$-(uridine-5'-)tetraphosphate; $P^1,P^4$-di(3'-azido-3'-deoxythymidine-5'-)tetraphosphate; $P^1,P^4$-di(3'-azido-3'-deoxythymidine-5'-)tetraphosphate; 2'(3')-benzoyl-$P^1,P^4$-di(uridine-5'-)tetraphosphate; $P^1,P^4$-di(2'(3')-benzoyluridine-5'-)tetraphosphate; $P^1$-(2'-deoxyguanosine-5'-)$P^4$-(uridine-5'-)tetraphosphate; $P^1$-(2'-deoxyadenosine-5'-)$P^4$-(uridine-5'-)tetraphosphate; $P^1$-(2'-deoxyinosine-5'-)$P^4$(uridine-5'-) tetraphosphate; $P^1$-(2'-deoxycytidine-5'-)$P^4$(uridine-5'-) tetraphosphate; $P^1$-(8-azaadenosine-5'-)$P^4$-(uridine-5'-) tetraphosphate; $P^1$-(6-mercaptopurineriboside-5'-)$P^4$-(uridine-5'-)tetraphosphate; $P^1$-(6-mercaptopurineriboside-5'-)$P^4$-(2'-deoxyuridine-5'-)tetraphosphate; $P^1$-(4-thiouridine-5'-)$P^4$-(arabinocytidine-5'-)tetraphosphate; $P^1$-(adenosine-5'-)$P^4$-(4-thiomethyluridine-5'-)tetraphosphate; $P^1$-(2'-deoxyadenosine-5'-) $P^4$-(6-thiohexylpurineriboside-5'-)tetraphosphate and $P^1$-(6-decyloxypurineriboside-5'-)$P^4$-(uridine-5'-)tetraphosphate.

18. The method according to claim 16, wherein said dinucleoside polyphosphates of general Formula I are dinucleoside triphosphates selected from a group consisting of: $P^1,P^3$-di(uridine5'-)triphosphate; $P^1$-(cytidine-5'-)$P^3$-(uridine-5')triphosphate; $P^1,P^3$-di(adenosine-5'-)triphosphate; $P^1$-(adenosine-5'-)$P^3$-(uridine-5'-) triphosphate; $P^1$-(adenosine-5'-)$P^3$-(cytidine-5'-)triphosphate; $P^1,P^3$-di(ethenoadenosine)triphosphate; $P^1$-(uridine-5'-)$P^3$-(thymidine-5'-)triphosphate; $P^1$-(adenosine-5'-)$P^3$-(inosine-5'-)triphosphate; $P^1,P^3$-di(uridine-5'-)$P^2,P^3$-methylenetriphosphate; $P^1,P^3$-di(uridine-5'-)$P^2,P^3$-difluoromethylenetriphosphate; $P^1,P^3$-di(uridine-5'-)$P^2,P^3$-imidotriphosphate; $P^1,P^3$-di(4-thiouridine-5'-)triphosphate; $P^1,P^3$-di(3,N$^4$-ethenocytidine-5'-)triphosphate; $P^1,P^3$-di(imidazo[1,2-c]pyrimidine-5(6H)-one-2-(3-nitro)-phenyl-6-β-D-ribofuranoside-5'-)triphosphate; $P^1$-(inosine-5'-)$P^3$-(uridine-5'-)triphosphate; $P^1$-(4-thiouridine-5'-)$P^3$-(uridine-5'-)triphosphate; $P^1$-(cytidine-β-D-arabinofuranoside-5'-)$P^3$-(uridine-5')triphosphate; $P^1$-(uridine-5'-)$P^3$-(xanthosine-5'-)triphosphate; $P^1$-(2'-deoxyuridine-5'-)$P^3$-(uridine-5'-) triphosphate; $P^1$-(3'-azido-3'-deoxythymidine-5'-)$P^3$-(uridine-5'-)triphosphate; $P^1,P^3$-di(3'-azido-3'-deoxythymidine-5'-)triphosphate; 2'(3')-benzoyl-$P^1,P^3$-di(uridine-5'-)triphosphate; $P^1,P^3$-Di(2'(3')-benzoyluridine-5'-)triphosphate; $P^1$-(2'-deoxyguanosine-5'-)$P^3$-(uridine-5'-) triphosphate; $P^1$-(2'-deoxyadenosine-5'-)$P^3$-(uridine-5'-) triphosphate; $P^1$-(2'-deoxyinosine-5'-)$P^3$-(uridine-5'-) triphosphate; $P^1$-(2'-deoxycytidine-5'-)$P^3$-(uridine-5'-) triphosphate; $P^1$-(4-thiouridine-5'-)$P^3$-(uridine-5'-) triphosphate; $P^1$-(8-azaadenosine-5'-)$P^3$-(uridine-5'-) triphosphate; $P^1$-(6-mercaptopurineriboside-5'-)$P^3$-(uridine-5'-)triphosphate; $P^1$-(6-mercaptopurineriboside-5'-)$P^3$-(2'-deoxyuridine-5'-)triphosphate; $P^1$-(4-thiouridine-5'-)$P^3$-(arabinocytidine-5'-)triphosphate; $P^1$-(adenosine-5'-)$P^3$-(4-thiomethyluridine-5'-)triphosphate; $P^1$-(2'-deoxyadenosine-5'-)$P^3$-(6-thiohexylpurine riboside-5'-)triphosphate; and $P^1$-(6-nonyloxypurineriboside-5'-)$P^3$-(uridine-5'-)triphosphate.

19. The method according to claim 16, wherein said dinucleoside polyphosphates of general Formula I are selected from a group consisting of: $P^1$-(uridine-5'-)$P^2$-(4-thiouridine-5'-)diphosphate; $P^1,P^5$-di(uridine-5'-)pentaphosphate; and $P^1,P^6$-di(uridine-5'-)hexaphosphate.

* * * * *